United States Patent [19]
Tomer

[11] Patent Number: 5,876,357
[45] Date of Patent: Mar. 2, 1999

[54] UTERINE CERVIX DILATION, EFFACEMENT, AND CONSISTENCY MONITORING SYSTEM

[75] Inventor: David Tomer, Haifa, Israel

[73] Assignee: Labor Control System (L.C.S.) Ltd., Nesher, Israel

[21] Appl. No.: 974,982

[22] Filed: Nov. 20, 1997

[51] Int. Cl.$^6$ .................................................. A61B 5/103
[52] U.S. Cl. .......................................... 600/591; 600/587
[58] Field of Search ................................... 600/551, 587, 600/591; 73/573, 789, 770

[56] References Cited

U.S. PATENT DOCUMENTS

| | | | |
|---|---|---|---|
| 4,141,345 | 2/1979 | Allen et al. | 600/591 |
| 4,432,376 | 2/1984 | Huszar | 600/591 |
| 4,476,871 | 10/1984 | Hon | 600/591 |
| 4,541,439 | 9/1985 | Hon | 600/591 |
| 5,183,055 | 2/1993 | Seager | 600/587 |
| 5,406,961 | 4/1995 | Artal | 600/591 |
| 5,438,996 | 8/1995 | Kemper et al. | 600/591 |
| 5,450,857 | 9/1995 | Garfield et al. | 600/591 |

*Primary Examiner*—Max Hindenburg
*Assistant Examiner*—Charles Marmor, II
*Attorney, Agent, or Firm*—Mark M. Friedman

[57] ABSTRACT

A system and method for monitoring uterine cervical dilation, effacement, and consistency during labor. A probe comprising a linear caliper and a flexible membrane is applied to the uterine cervix, and loaded by a constant closing force generated by a hydraulic piston mechanism. The flexible membrane assumes the contour of the opening of the uterine cervix, a fiber-optic sensor on the probe measures the curvature of the membrane, and a processor calculates cervical dilation from the degree of curvature of the membrane. The displacement of the caliper arms is recorded, and a processor calculates the degree of cervical effacement from the displacement data. The caliper closing force is transiently altered, and the resultant caliper arm displacement value is compared with a baseline displacement value so as to calculate a descriptor of cervical consistency. Cervical dilation, effacement and consistency data is displayed in real time, and compared with stored normal values.

20 Claims, 13 Drawing Sheets

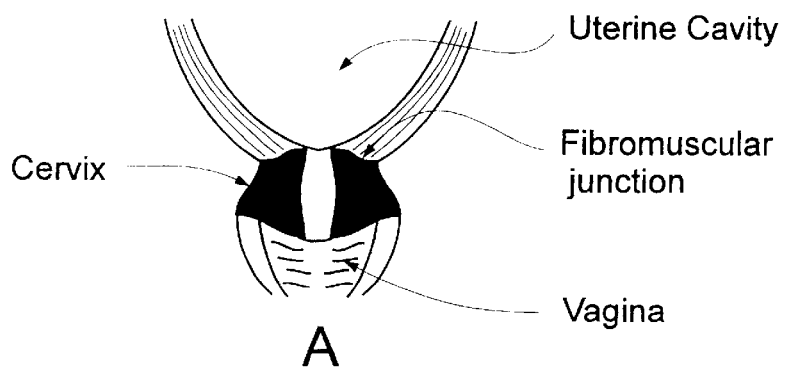
Fig. 1a
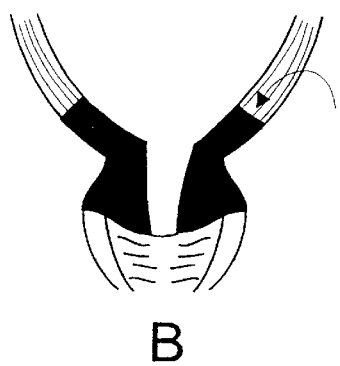
Fig. 1b
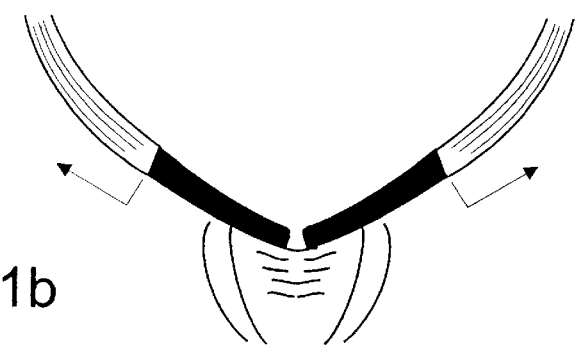
Fig. 1c
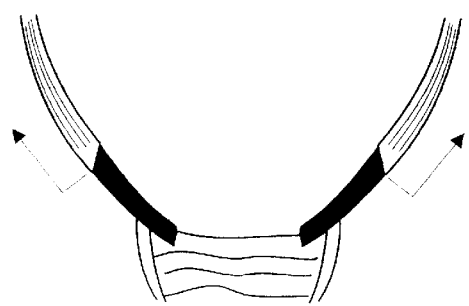

Fig. 2

UTERINE CERVIX DILATION, EFFACEMENT, AND CONSISTENCY MONITORING SYSTEM

FIELD AND BACKGROUND OF THE INVENTION

The present invention relates to the field of medical monitoring instrumentation in general, and in particular, to the field of labor monitoring devices.

It is well known that the process of labor and childbirth entails the gradual thinning and dilation of the uterine cervix, in response to coordinated uterine contractions, resulting in the eventual expulsion of the fetus through the fully dilated uterine cervix and birth canal. As such, the degree, and rate of progression, of cervical thinning and dilation is closely monitored by hospital staff during labor and childbirth, and is considered to be the cardinal indicator of the progression of labor. Slow or inadequate cervical thinning and dilation may indicate inefficient or pathological labor, and is often an indication for medical or surgical intervention, particularly if accompanied by evidence of fetal distress.

FIG. 1 demonstrates the normal process of cervical dilation and thinning. As can be seen, the cervix thins and dilates as it is "pulled up" into the uterus. Although the normal gravid cervix is slightly soft to the touch, it remains thick, rigid, and closed until a few weeks before the end of gestation, measuring approximately 2–3 cm in length. Several weeks before the onset of labor, the cervix begins to become perceptibly softer. During the process of active labor, the cervix becomes progressively softer and thinner, a process known as effacement. As effacement progresses, the cervix also gradually dilates. Dilation does not ordinarily proceed at a constant rate. Typically, dilation is slow until 4–5 cm dilation is reached, more rapid until dilation is nearly complete, and then slower again until full dilation of 10 centimeters is achieved. Thereafter, the second stage of labor, during which the fetus passes through the dilated cervix and birth canal, begins.

Cervical dilation is recorded in centimeters. Effacement of the cervix is recorded as a percentage: an uneffaced (0%) cervix is firm and about 2.5 cm long; 50% effacement implies that the cervix is about 1 cm thick and somewhat softer; a completely effaced cervix (100%) is soft and only a few millimeters thick. In addition, the consistency of the cervix to touch during manual vaginal examination, that is, whether it is firm or soft, is also an indicator of the process of effacement. Measuring the actual transmural thickness of the wall of the cervix, that is, from the endocervical or uterine surface to the outer vaginal surface, in millimeters, would provide a precise and accurate description of the degree of cervical effacement, however such evaluation is often not feasible by manual vaginal examination.

Due to its cardinal importance as an indicator of the progress of labor, the amount of cervical dilation and effacement is regularly determined by professional attendants (such as midwives and obstetricians) during the course of labor. On average, ten manual vaginal examinations are required per labor. The data is usually plotted on a labor observation chart, as illustrated in FIG. 2. On the illustrated chart, "station" refers to a description of the location of the fetal head in relation to the maternal pelvis. It can be seen that cervical dilation progresses as the fetus descends through the maternal pelvis.

Manual vaginal examinations, however, suffer from several disadvantages: they are embarrassing and uncomfortable for the patient, subjective, inaccurate, provide very intermittent information, can introduce infection into the uterus, require manual charting, and add to the medical staff workload.

Although several monitoring devices are routinely used during the course of labor (such as fetal heart rate monitors, fetal oxygen saturation monitors [pulse oxymetry], uterine activity monitors [tocometry], and maternal vital signs monitors), automatic monitoring of cervical dilation and effacement is not yet available. This is despite the fact that several methods for measuring cervical dilation have been described. These methods include:

1) Obstetric gloves incorporating a measuring string or measuring tape.

2). Finger mounted angular V calipers.

This device is attached to the obstetricians fingers, and is inserted into the vagina whenever a measurement is required. The obstetrician measures dilation by spreading his fingers in the same way as done in regular manual vaginal examination. A mechanical scale, potentiometer, or strain gauge measures the angle between the caliper arms, and the measurement is converted to a dilation value. Both of the above devices suffer from the deficiencies described above for standard manual vaginal examinations.

3) Cervix mounted angular V calipers.

This device is placed in the vagina and attached to two points on opposite sides of the cervix to each other. A mechanical scale, potentiometer, or strain gauge then measures the angle between the caliper arms, and the measurement is converted to a dilation value. This device suffers from the deficiency that is substantially occupies the vagina, thus interfering with other monitoring and treatment activities. It therefore has to be removed and reinserted repeatedly. In addition, it is uncomfortable to the patient, may require manual charting, and is difficult to install, thus adding to the medical staff workload.

4) Induction transmitters and receivers clamped to two sides of the cervix opposite to each other.

As the distance between the primary and secondary induction windings affects the induced signal, the distance between them (which is equal to the cervical diameter) can be measured. This device suffers from the deficiency that it functions effectively only until about 5–7 cm dilation, whereas manual measurements are required until 10 cm dilation. In addition, the insertion of other instruments into the vagina and the cervix, as is often done during labor, adversely effects the measurement readings of the device, rendering it impractical for clinical use.

5) A multi-switch membrane that is inserted into the uterus, and pressed between the cervical internal os and the fetal head.

As the switches in the cervical opening are not pressed, while those within the uterus are, an ongoing indication of the progress of dilation is rendered. This device suffers from several deficiencies. Firstly, it is necessary to insert the membrane between the fetus and the uterine wall, which is technically difficult, particularly before the amniotic sack has ruptured, and undesirable afterwards due to the risk of introducing infection. Secondly, the membrane often shifts, giving rise to false measurements. In addition, as the membrane crosses the cervix from one side to the other after placement, the entrance to the uterus is obstructed, thus interfering with other monitoring and treatment activities. Other disadvantages are that the device is uncomfortable for the patient, and adds to the medical staff workload.

6) Untrasound visualization of the cervix.

Ultrasound monitoring of cervical dilation suffers from the following deficiencies: the probe inserted into the vagina is relatively large (and thus must be removed to allow other monitoring and treatment activities), the ultrasound machine is expensive and complicated to operate, ultrasound radiation that is applied for many hours represents a potential hazard to the fetus, the probe is uncomfortable for the patient, the device is inaccurate, and the device can introduce infection into the uterus.

There is therefore a need for an instrument which is capable of continuously, accurately, and automatically monitoring and recording the progress of cervical dilation and effacement. Such an instrument should be safe, easily installable, and comfortable to the mother. Furthermore, such an instrument should not interfere with other monitoring or treatment procedures commonly performed during labor.

SUMMARY OF THE INVENTION

The current invention is a real time labor monitoring system. A probe, in the form of a linear caliper-clamp apparatus and a flexible membrane, is manually inserted into the vagina and clamped onto the wall of the cervix, such that the arms of the caliper straddle the thickness of the cervical well, and the flexible membrane approximates the radius of curvature of the opening of the cervix. The linear caliper arms are loaded by a uniform closing force, such that the gap between them follows the cervical thickness. A combined hydraulic and spring (or weight) mechanism applies the closing force and also measures the displacement of the arms of the caliper relative to each other. This displacement is depicted by the movement of a piston located in a control unit, which is external to the patient. A sensor in the control unit measures the displacement of the piston, which is then translated, by a labor room computer processor connected to the control unit, or by a processor in the control unit itself, into a descriptor of effacement. An electrical sensor mechanism measures the curvature of the flexible membrane adherent to the cervix, and relays such data to the control unit. The labor room computer processor connected to the control unit, or the processor in the control unit itself, uses the membrane curvature data to calculate the dilation of the cervix. Finally, the closing force applied to the cervix by the calipers is transiently altered by the control unit, resulting in a new piston displacement value being acquired. The labor room computer processor, or the processor in the control unit itself, compares the new piston displacement and corresponding closing force values to the previous piston displacement and closing force values (all values having been acquired while the cervix was at the same degree of effacement), and calculates therefrom a descriptor of cervical firmness or softness, hereinafter referred to as a descriptor of cervical consistency. A labor room computer display depicts the ongoing cervical dilation, effacement, and consistency data in real time in textual, in numerical, and in graphical chart formats. A memory bank in the labor room computer is automatically accessed so as to compare the actual progress of cervical dilation and effacement with previously defined desired patterns for the progress of labor. If necessary, the labor room computer automatically alerts the medical staff to any deviations from normal labor patterns, by means of audio and/or visual signals on the display. Probable causes for such deviations are retrieved from the computer memory and displayed on the monitor, along with possible appropriate therapeutic maneuvers. Other labor monitoring data form standard labor monitoring devices may be input to the computer (for example, using communications protocol RS232) for display on the monitor, as may be demographic data derived from an external source, such as a hospital mainframe computer database. The labor room computer may relay labor progress data to a central control station computer (located, for example, at a nurses station), which is monitoring data from multiple control units/labor room computers (each of which is located, for example, in an individual labor/delivery room). The central control station computer can perform identical functions to those of the labor room computer. The central control station computer may receive data input via modem from an autonomous monitoring system control unit (identical to the above described labor room computer and control unit combination) located outside of the hospital, for example in a patients house. This can be helpful in the beginning of labor, as the system can help the patient decide when true labor has begun. The data modem transmission option can give medical staff at the hospital the option of monitoring the progress of expecting mothers who are still at home. In addition, control unit data can be transmitted, via modem, to distant locations, thus facilitating detailed consultation with medical staff outside of the hospital or in remote hospitals.

All data processed by the labor room computer/control unit or central control station computer may be printed out on a connected printer, or stored on a conventional storage system such as an optical disk. Information for each labor room can be displayed in abridged form on the monitor of the central control station computer, such that the progress of labor in all labor rooms in a delivery ward can be simultaneously appreciated, or complete monitoring data for any given labor room can be called up, so as to focus on one patient only.

It is therefore an object of the current invention to provide a labor monitoring system which continuously and automatically monitors the progress of cervical dilation, effacement, and consistency.

It is a further object of the current invention to provide a labor monitoring system which is safe to the mother and fetus.

It is a still further object of the current invention to provide a labor monitoring system which is easily installable, comfortable, and not embarrassing for the mother.

It is yet a further object of the current invention to provide a labor monitoring system which does not interfere with other monitoring or treatment procedures commonly performed during labor.

According to the teachings of the present invention there is therefore provided a cervical dilation, effacement, and consistency monitoring system, including a membrane, operative to flex in accordance with a curvature of a cervix, and a first sensor, operative to sense a degree of flexion of the membrane and generate a first signal describing the degree of flexion.

There is further provided a method for measuring uterine cervical dilation, effacement, and consistency, including the steps of providing a membrane, operative to flex in accordance with a curvature of a cervix; sensing a degree of flexion of the membrane; generating a first signal describing the degree of flexion; and processing the first signal so as to generate a parameter describing a degree of uterine cervical dilation.

BRIEF DESCRIPTION OF THE DRAWINGS

The invention is herein described, by way of example only, with reference to the accompanying drawings, wherein:

FIG. 1 is an illustration of the process of cervical dilation and effacement.

Figure 2:
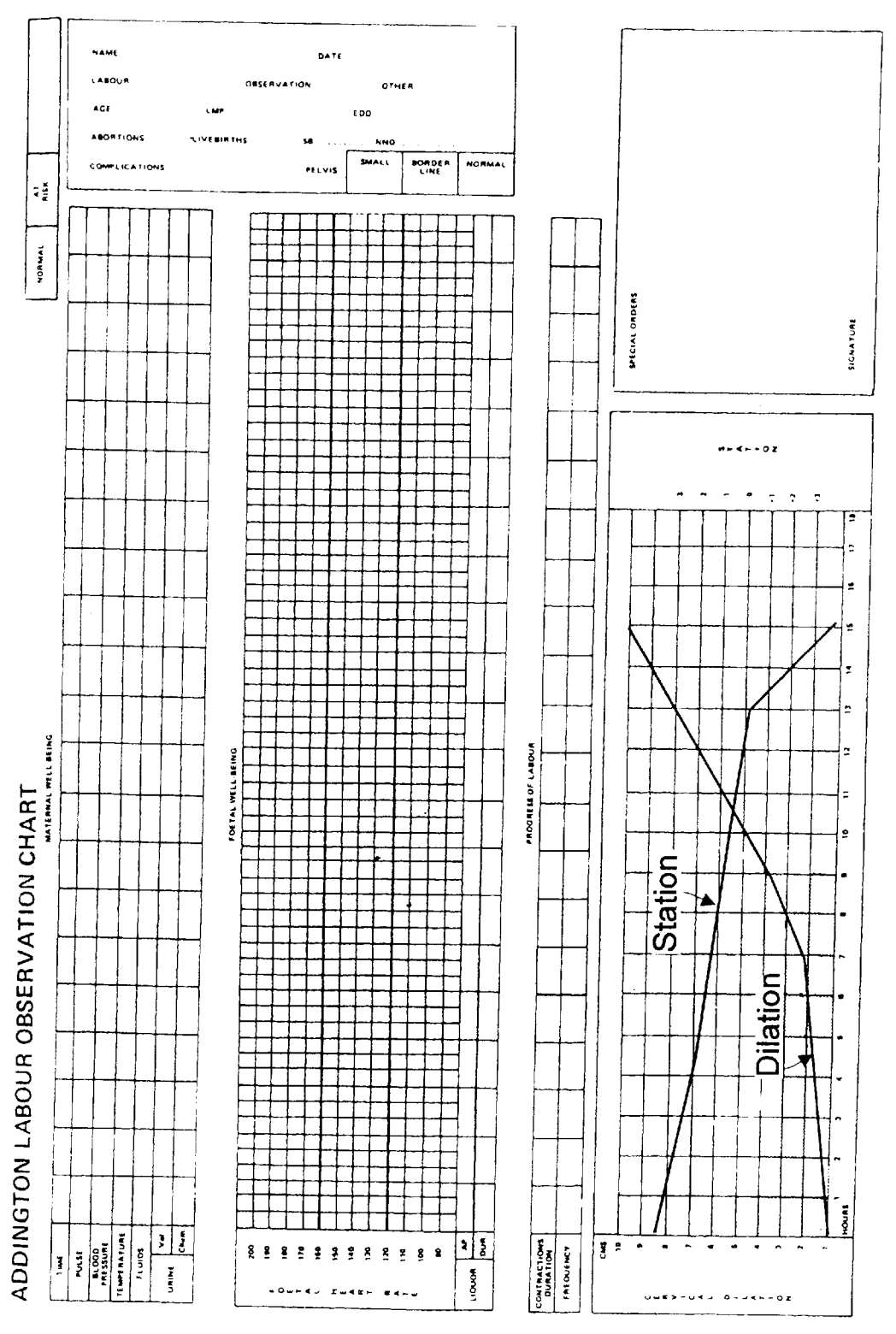

FIG. 2 is an example of a labor observation chart.

FIG. 11 includes a top view of the device.

DESCRIPTION OF THE PREFERRED EMBODIMENT

The present invention is a system and method for monitoring the dilation, effacement, and consistency of the uterine cervix during labor.

The principles and operation of a uterine cervix dilation, effacement, and consistency monitoring system, according to the present invention, may be better understood with reference to the drawings and the accompanying description.

Figure 3:
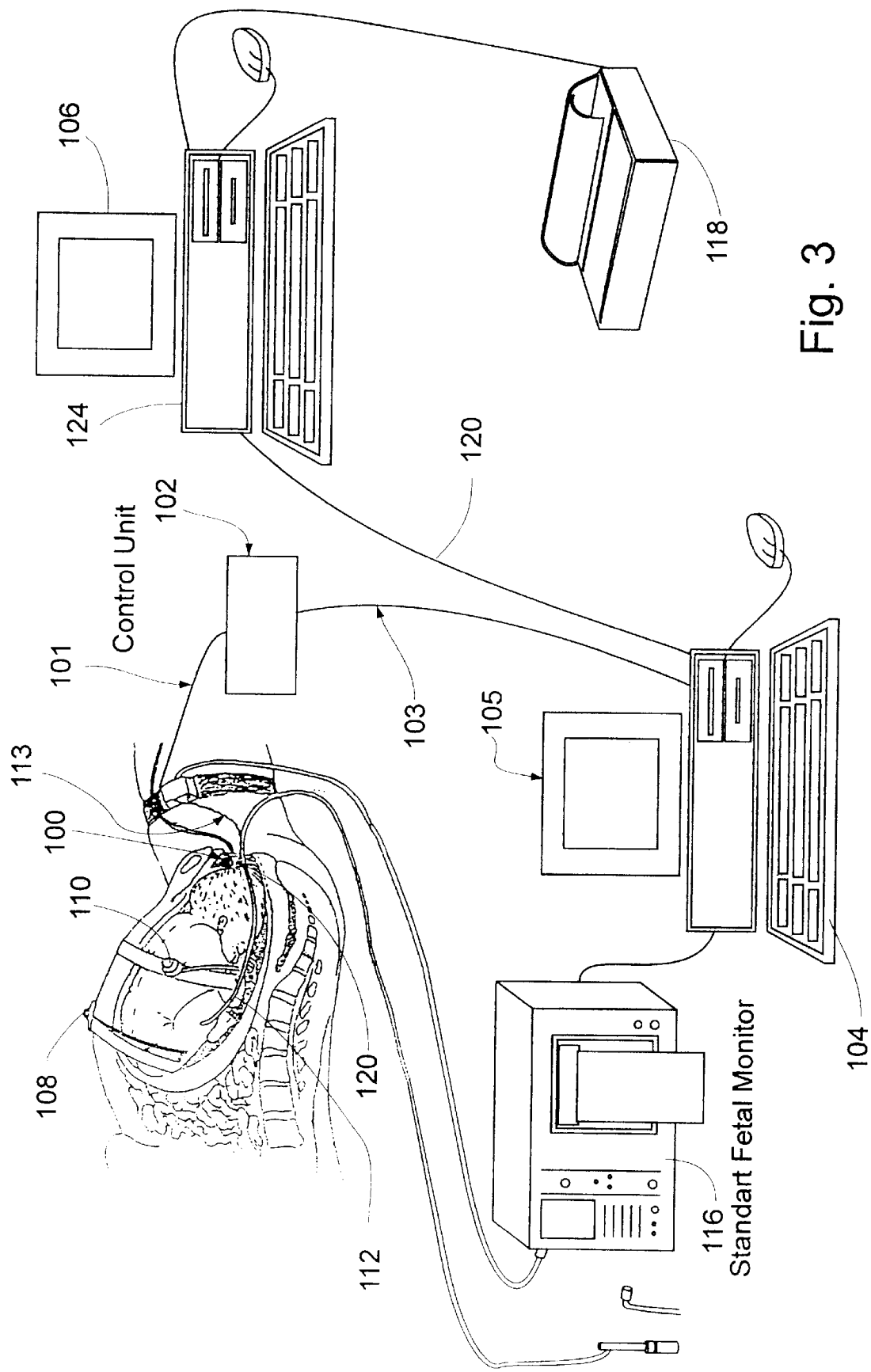
FIG. 3 is a schematic diagram of the overall organization of a labor monitoring system.

Turning now to the figures, FIG. 3 is a schematic diagram of the overall organization of a uterine cervix dilation, effacement, and consistency monitoring system according to the present invention.

A cervical probe 100 is attached to a cervix 126 of a patient. Probe 100 is connected to a control unit 102 via a connector 101. Connector 101 includes cable, hydraulic, pneumatic and/or fiber-optic elements (not shown), as detailed below in FIGS. 9, 10, 11, 12, and 13. Control unit 102 receives data describing the physical status of probe 100, translates such data into data describing cervical radius of curvature and thickness, and transmits such data to a labor room computer 104, via a connector cable 103. In an alternative embodiment, control unit 102 and labor room computer 104 may be integrated into one physical unit. Labor room computer 104 processes the data received from control unit 102, using standard software algorithms which are well known in the art, to calculate the degree of dilation of cervix 126, the degree of effacement of cervix 126, and the consistency of cervix 126. Labor room computer 104 displays this data on a display 105. Display 105 depicts the ongoing cervical dilation, effacement, and consistency in real time in textual, in numerical, and in graphical chart format. Labor room computer 104 also contains a memory bank (not shown) storing previously defined desired patterns for the progress of labor. This memory is accessed by labor room computer 104, so as to compare the actual progress of cervical dilation and effacement with the desired patterns. Labor room computer 104 automatically alerts the medical staff to any deviations from normal labor patters, by means of audio and/or visual signals on the display. Probable causes for such deviations are retrieved from the memory of labor room computer 104 and displayed on display 105, along with possible appropriate therapeutic maneuvers (which are stored in the memory of labor room computer 104).

Labor room computer 104 may also receive data input from standard labor monitoring devices such as uterine contraction and fetal heart rate monitor 116, which is connected to the patient via sensors 108, 110, 112, and 113. This data may also be displayed on display 105.

Labor room computer 104 is optionally connected to a central control station computer 124, via connector cable 120. Central control station computer 124 can perform all functions described for labor room computer 104, and can be optionally connected directly to control unit 102. Central control station computer 124 may receive input from multiple labor room computers 104 or control units 102 (not shown), or from remote labor room computer/control units connected to central control station computer 124 via a network or modem (not shown). Central control station computer 124 has a display 106 for displaying data received from all the above mentioned sources. A printer 118 connected to central control station computer 124, or optionally to labor room computer 104, can print out labor monitoring data.

The system in each labor room (that is, control unit 102 and labor room computer 104) can operate autonomously and is not necessarily dependent on central control station computer 124. Central control station computer 124 can communicate with each one of the individual labor room monitoring systems, and display simultaneously the data regarding all labor rooms, or "zoom-in" onto the data from a specific labor room.

Labor room computer 104 and central control station computer 124 are standard personal computers, with at least a 386 CPU processor and 4 megabytes of RAM, running standard operating systems.

Figure 4:
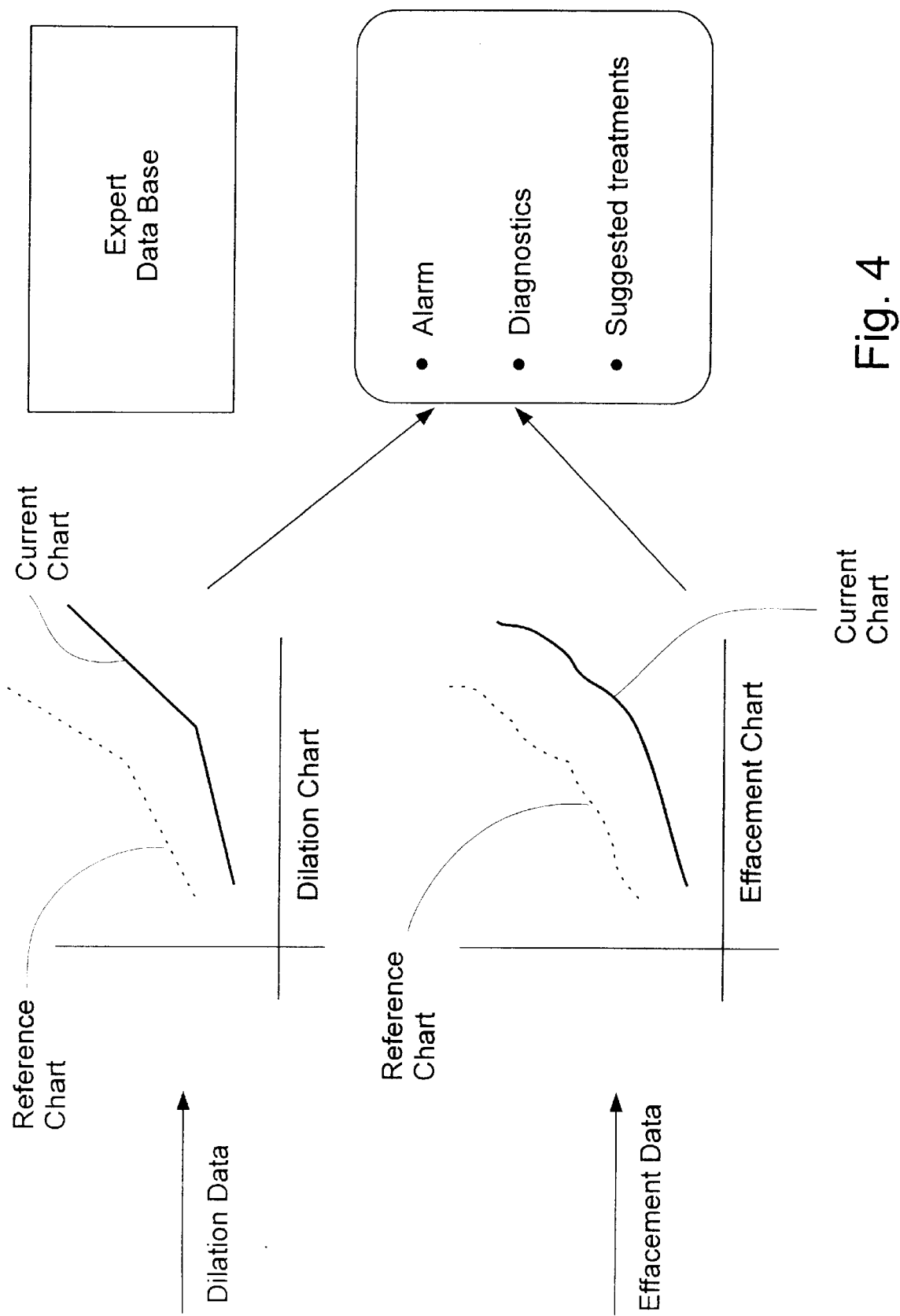
FIG. 4 shows an example of graphic displays.

FIG. 4 shows an example of graphic displays depicted on display 105 or 106. Cervical dilation or effacement data is depicted graphically as a current chart, along with a reference chart for comparison, derived from the memory of computers 104 or 124. In the event that the current chart deviates significantly from the reference chart, computers 104 or 124 access a data base, retrieve appropriate data, and display a list of appropriate diagnoses and suggested treatments on displays 105 or 106. A warning alarm is also displayed.

Figure 5:
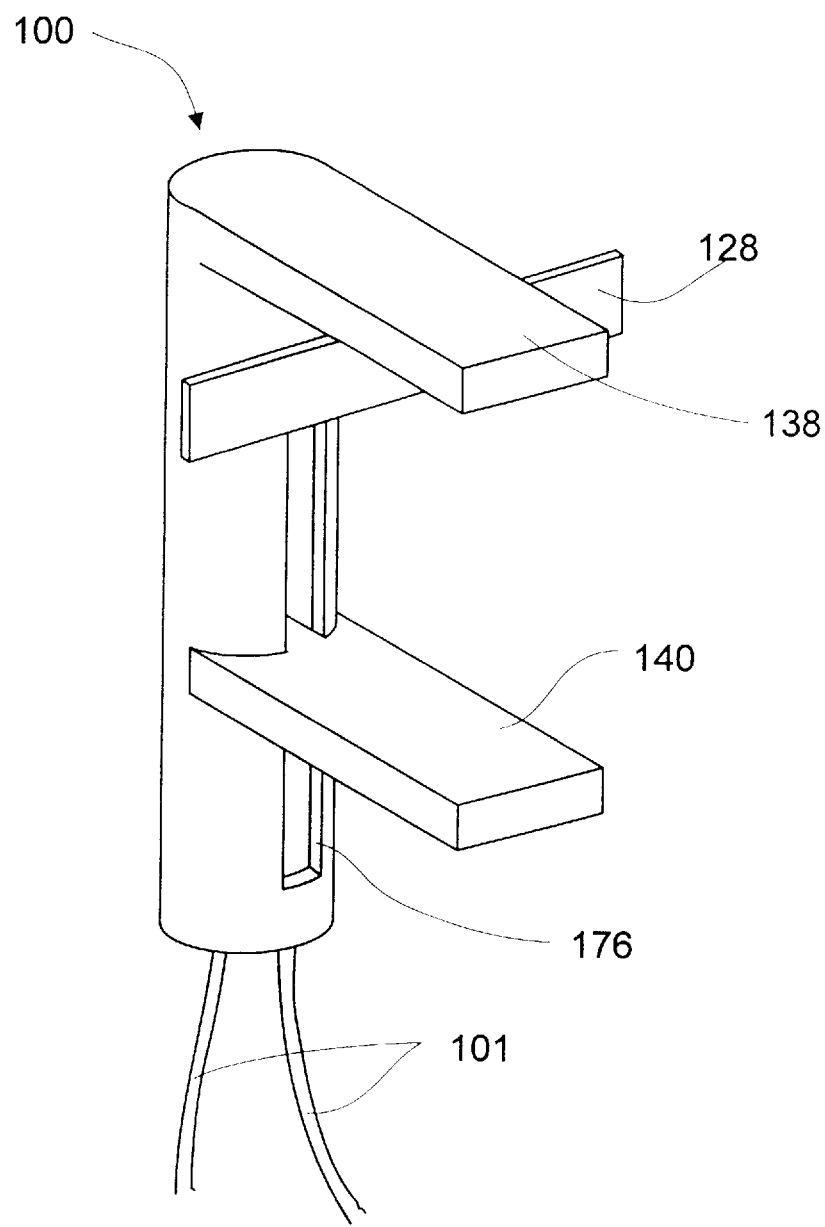
FIG. 5 is an illustration of the cervical dilation, effacement, and consistency probe.
Figure 6:
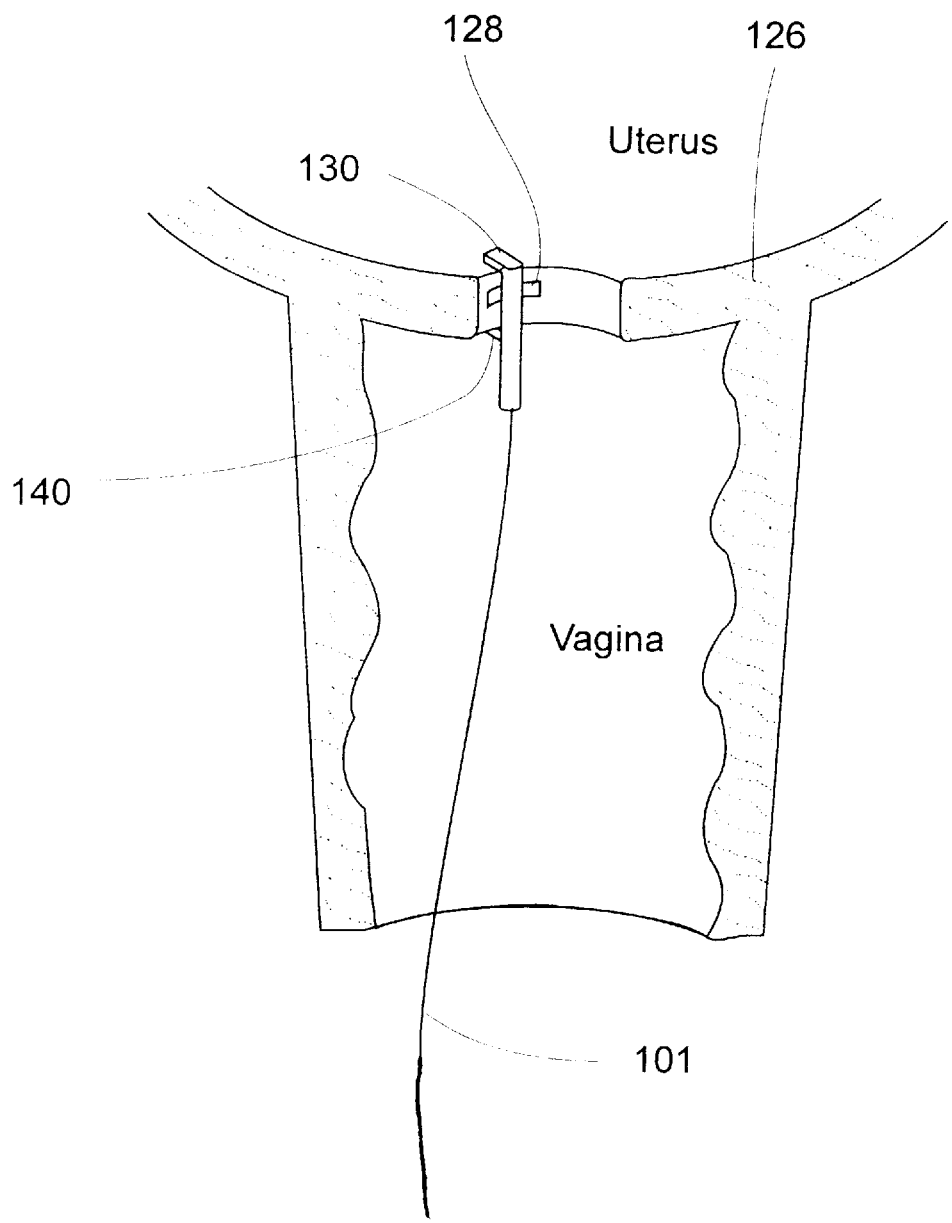
FIG. 6 is an illustration showing how the probe is installed on the uterine cervix.

FIG. 5 shows an illustration of the exterior of probe 100, and FIG. 6 demonstrates how probe 100 is positioned on cervix 126. Probe 100 has two basic parts:

1) A flexible membrane 128. By "flexible" is meant that the material is able to bend easily, but still has enough resilience to regain its original shape when external bending forces are removed or diminished. By "membrane" is meant a flexible material of approximate dimensions of 20×5 mm and up to about 1 mm thick, made of any material (stainless steel, plastic, etc.) with high enough yield strength to avoid any residual plastic deformation after being bent for insertion into the minimal diameter of cervix 126. Membrane 128 is thus a thin membrane that is attached to cervix 126 and is forced to bend at the same radius of curvature as the opening of cervix 126. The curvature of membrane 128 is measured by a sensor (not shown) and translated into the diameter of cervix 126, which is equivalent to the dilation of cervix 126, by computer 104 or 124, or by a processor in control unit 102.

2) Linear-caliper arms 138 and 140. Arm 138 is fixed and immobile on probe 100, while arm 140 is mobile on a guide-rail 176. Caliper arms 138 and 140 are loaded by a uniform closing force, generated by a mechanism described in FIGS. 9, 10, 11, 12, and 13 below, such that the gap between caliper arms 138 and 140 represents and follows the transmural cervical thickness, which is proportional to the effacement and the consistency of cervix 126. Caliper arms 138 and 140 are built from any suitable plastic or metal material. Caliper arms 138 and 140 perform three functions: they clamp probe 100 to cervix 126, they press membrane 128 against the surface of cervix 126, such that it is fixed to the surface and forced to bend to the same radius of curvature as the opening of cervix 126, and they describe the thickness of cervix 126 by their displacement. By "fixed" is meant that the membrane, along its entire length, remains substantially in contact with the surface of cervix 126, adopting the same radius of curvature as that of the surface of cervix 126.

Figure 7:
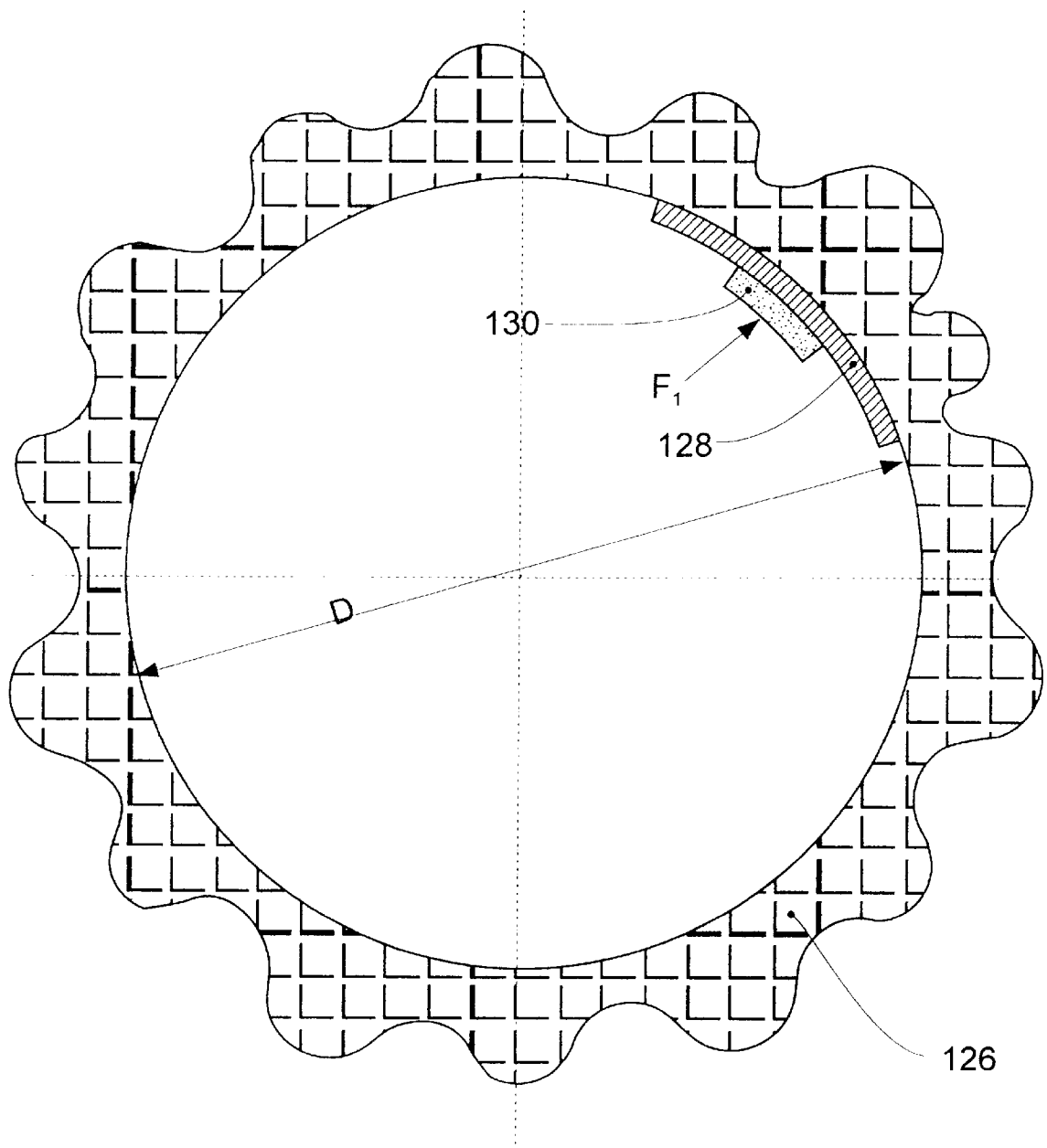
FIG. 7 is an illustration of the principle of cervical dilation measurement by a flexible membrane.

FIG. 7 illustrates the principles of cervical dilation measurement by membrane 128. The degree of dilation of cervix 126 is derived from a measurement of the diameter (D) of the cervical opening. Attachment of membrane 128 to a circle, for example the inner surface of cervix 126, is achieved by applying a force F1 to the center of membrane 128. This will obligate membrane 128 to fit the circumference of cervix 126 for the whole length of membrane 128. The deflection of membrane 128 is therefore a function of the radius of curvature of the circle—and thus of the diameter of the circle. The deflection of membrane 128 is measured by a sensor 130, located on probe 100. In the preferred embodiment, sensor 130 is a specially treated fiber optic wire, such as a Shape Sensor (Measurand Inc. Fredicton, NB, Canada) as described in U.S. Pat. Nos. 5,321,257, and 5,633,494, and in PCT/CA94/00314, and incorporated herein by reference. The fiber optic wires pass from cervix 126, in connector 101, through the vagina to outside of the woman's body. A standard A/D converter, located in control unit 102, processes the analog data output of sensor 130, and the digital information is relayed to computer 104 or 124. Alternatively, sensor 130 may be a strain gauge or a piezoelectric sensor.

Figure 8:
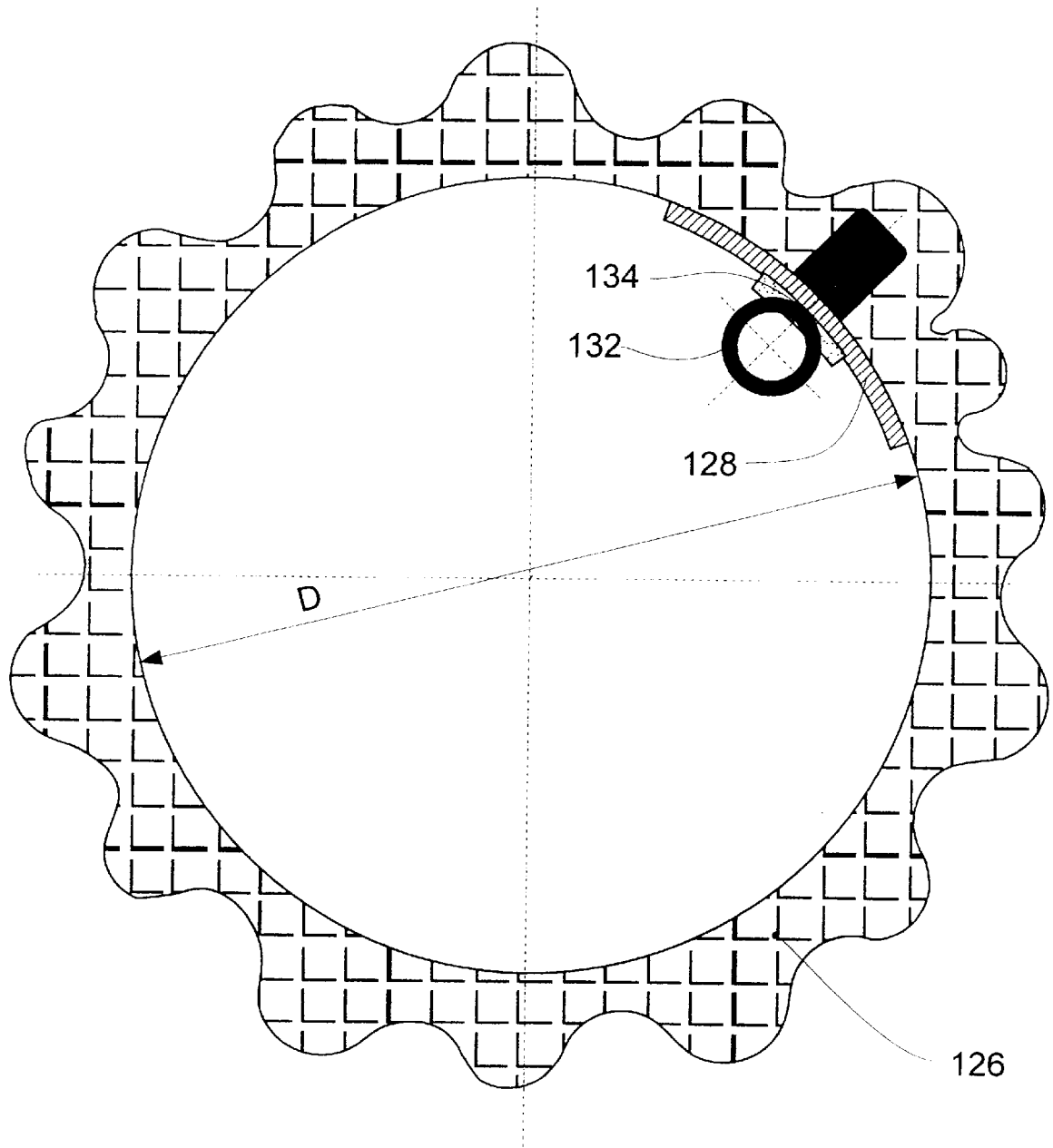
FIG. 8 is a schematic depiction of a method for fixing a flexible membrane onto the surface of a cervix.

FIG. 8 illustrates a method for fixing membrane 128 onto the surface of cervix 126. A clamp 132, that can be attached to cervix 126, holds membrane 128 against the surface of cervix 126, by applying pressure along a central line (or point) 134 of clamp 132. By clamp is meant an apparatus that clips to a part by inwardly pressing it from two opposite sides. In the preferred embodiment of the invention, clamp 132 is the same as a linear caliper containing arms 138 and 140, which are also used for effacement monitoring.

Figure 9:
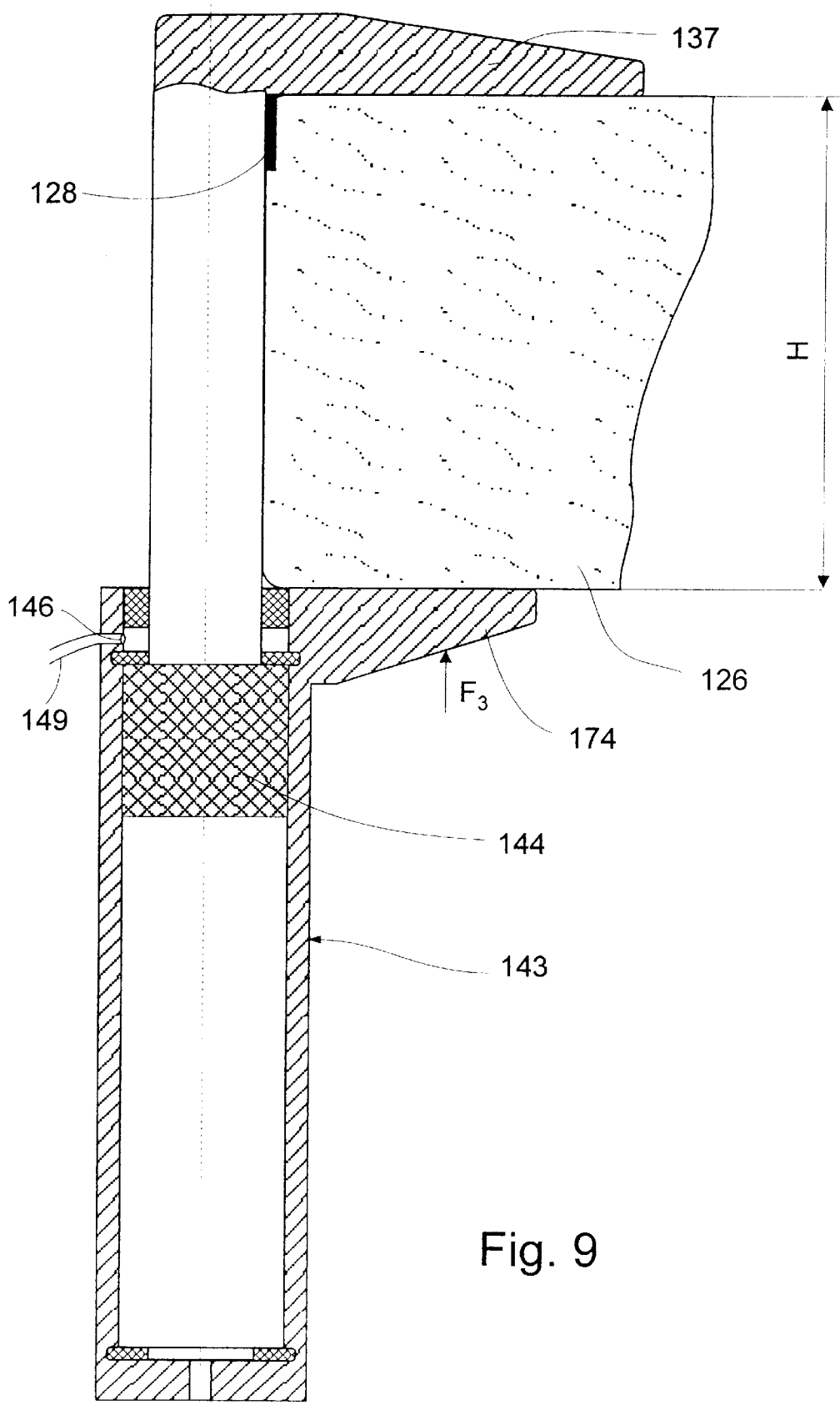
FIG. 9 is a diagram of the structure of a first embodiment of a linear caliper.

FIG. 9 is a diagram of the structure of a first embodiment of a linear caliper 143. By "linear caliper" is meant an instrument with two opposed parallel arms that can move with respect to one another, so as to allow measurement of the gap between them (and thus measurement of the thickness of the part being measured). Linear caliper 143 includes a casing 174 which is composed of a cylinder and an immobile fixed arm. A piston 144 is mobile within casing 174, and is attached to a caliper arm 137. Fluid from a hydraulic system centers the chamber of the cylinder of casing 174 via port 146. Increased fluid inflow via port 146 forces piston 144 down into the cavity of the cylinder of casing 174, thus moving caliper arm 137 closer to the fixed caliper arm integrated into casing 174, and generating a closing force F3.

In a preferred embodiment, remote control of caliper arm 137 is achieved by a hydraulic or pneumatic system, by a cable apparatus, or by other similar means, as described below in FIG. 10. Piston 144 is connected to an external piston (not shown), located in control unit 102, by a liquid-filled plastic tube 149 via port 146. This external piston is loaded by a constant force (either gravity, a low coefficient spring, or a pneumatic pressure). Measurement of the degree of effacement of cervix 126 is achieved by measuring the transmural thickness (H) of cervix 126, this being approximated by the distance between caliper arm 137 and casing 174. As the hydraulic fluid is not compressible, movement of the external piston mirrors that of caliper arm 137. The displacement of the external piston is measured by a standard translation sensor such as a linear variable differential transformer (LVDT) (Gulton-Stathan, Costa Mesa Calif., USA), a linear motion potentiometer (Sakae Tsushin Kogyo Co., Ltd., Kanagawa, Japan), or a linear digital encoder (RSF Electronics Fremont, Calif., USA), each of which generates analog or digital output that is fed into control unit 102 and then computer 104 or 124.

Figure 10:
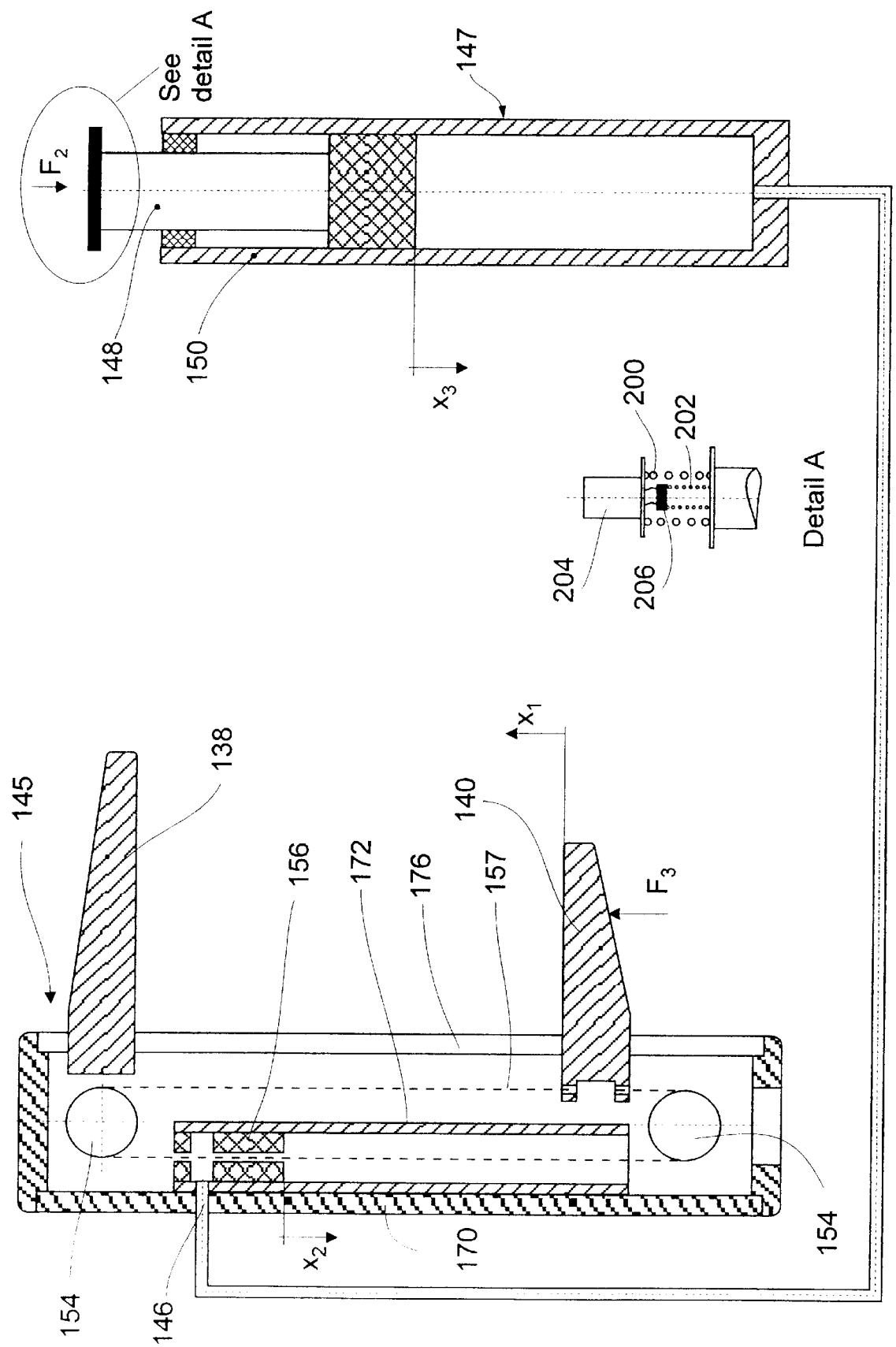
FIGS. 10 and 11 are diagrams of a second embodiment of a linear caliper and hydraulic system.
Figure 11:
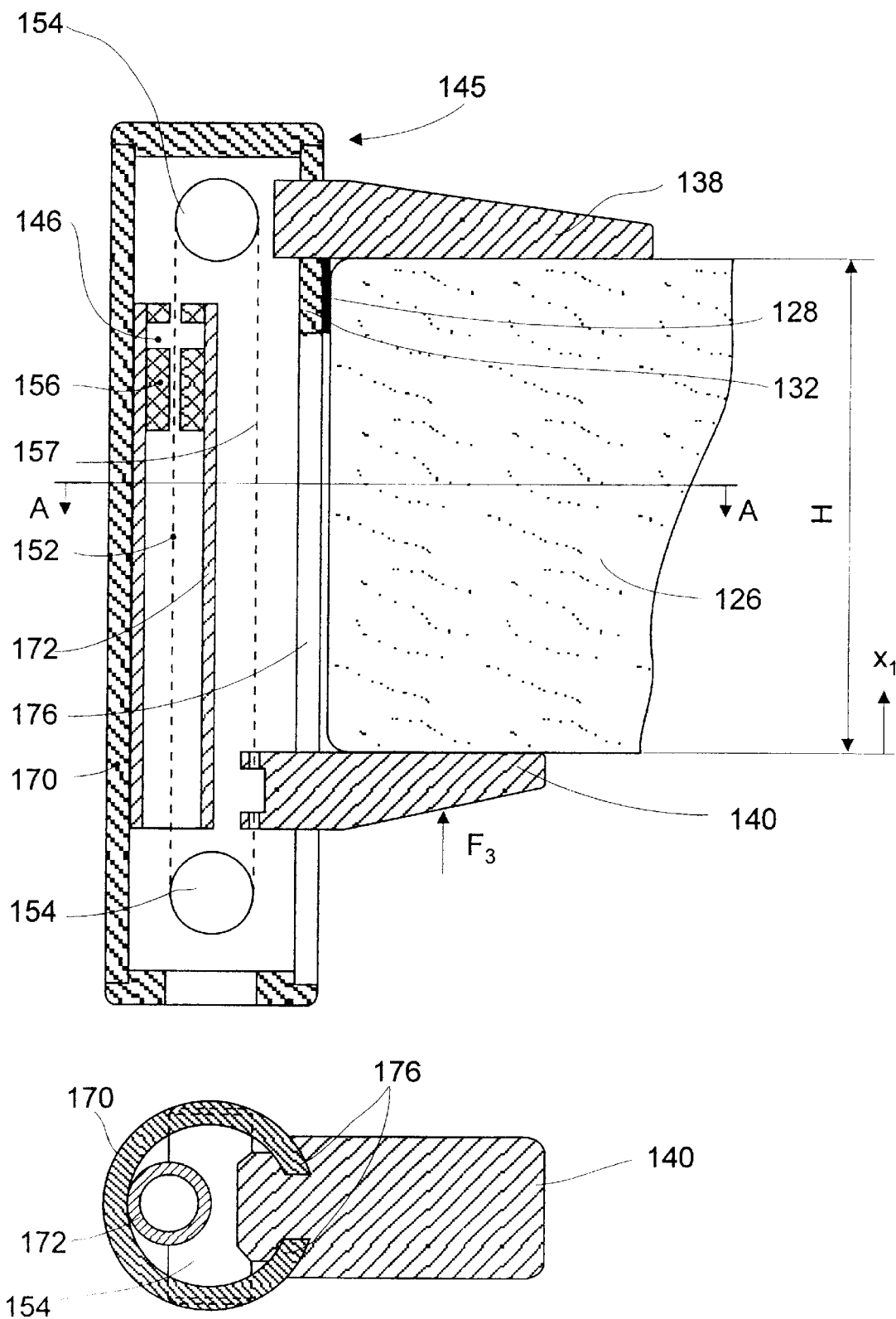

FIGS. 10 and 11 illustrate a second embodiment of a linear caliper and hydraulic system. A linear caliper 145 has two arms 138 and 140. Arm 138 is fixed to casing 170 of caliper 145, while arm 140 is mobile upon a guide rail 176. Arm 140 can be moved axially by a hydraulic fluid that exerts pressure on a piston 156. Piston 156 is suspended on a wire 157, which is also connected to arm 140. Wire 157 is taught, and wound over roller-pins 154. Piston 156 is contained within an internal cylinder 172, forming a sealed hydraulic/pneumatic system. The hydraulic fluid is in continuity, via port 146 and tube 149, with an external piston 147, which is located in control unit 102 (not shown). External piston 147 has a casing 150 enclosing a mobile piston 148.

A force F3 applied to cervix 126 is proportional to a force F2 generated in external piston 147. Thus, if force F2 is kept constant (by a weight, spring or other means), force F3 will also be constant, regardless of the displacement X1 between caliper arms 140 and 138. A displacement X3 of piston 148 is proportional to displacement X1, and is thus a means for remote measurement (i.e. in control unit 102) of the effacement H. Displacement X3 is measured visually or electrically means of a standard translation sensor such as a linear variable differential transformer, a linear motion potentiometer, or a linear digital encoder, each of which generates a digital output that is fed into computer 104 or 124.

Movement of piston 148 in the opposite direction (-X3) results in movement of piston 156 in an opening direction (-X2), and therefore opening of caliper arms 138 and 140 (-X1). This is useful for clamp installation and for clamp removal.

It should be noted that in linear caliper 145, as illustrated in FIG. 10, the piston mechanism is arranged parallel to the axis of movement of arms 138 and 140, whereas in linear caliper 143, as illustrated in FIG. 9, the piston mechanism is in tandem to the axis of movement of arms 137 and 174. Linear caliper 145 is thus shorter than linear caliper 143, and more suitable for use within the confines of the vagina.

The following description details the principles underlying the calculation and description of cervical consistency, as performed by means of a double force loading mechanism. It will be understood that if closing pressure F3 exerted by caliper arms 138 and 140 is not kept constant, but rather is increased or decreased, the displacement between arms 138 and 140 (H) will change. The extent to which H increases or decreases (as cervix 126 is "squashed" or "released" between arms 138 and 140) will depend on the firmness, or consistency, of the cervical tissue. Referring now to detail A in FIG. 10, a low coefficient spring 200 connected to piston 148 applies a constant force $F3_1$ to piston 148. This is the baseline condition under which cervical effacement is continuously monitored. The force applied by this type of spring is only minimally influenced by the deflection of the spring. As a result, clamping force $F3_1$ is almost uniform, regardless of the degree of cervical effacement. When it is desired to measure cervical consistency, a motor operated screw 206, attached to a motor 204, momentarily applies an additional force, such that a total force $F3_2$ is applied by the two springs together to piston 148, via a spring 202. By measuring thickness $H_1$ under force $F3_1$ and thickness $H_2$ under force $F3_2$ an index of consistency can be calculated as follows: for a given force change $F3_2-F3_1$ there will be respective deformation $H_2-H_1$. Assuming that $F3_2$ is larger than $F3_1$, $H_2$ should be smaller than $H_1$. A consistency coefficient is defined as:

$$\text{Consistency} = (F3_2 - F3_1)/(H_2 - H_1)$$

Alternatively, other definitions for consistency may be employed, such as $(H_1-H_2)$ for a given standard $F3_2$ and $F3_1$. The time gap between the two measurements must be kept short, so as to ensure that cervical consistency and effacement is uniform for both measurements.

A larger deformation implies a softer cervix. "Double loading" of piston 148 for the purpose of measuring consistency can be automatically performed at regular intervals by attaching a standard timing mechanism to motor 204, such that motor 204 becomes operative for a short period of time at predefined intervals. Alternatively, double loading of piston 148 can be performed manually by the operator. In either instance, the two sets of force and displacement data are input to control unit 102, or computer 104 or 124, which then calculates the above described consistency coefficient for display. Motor 204 is located in control unit 102.

Figure 12:
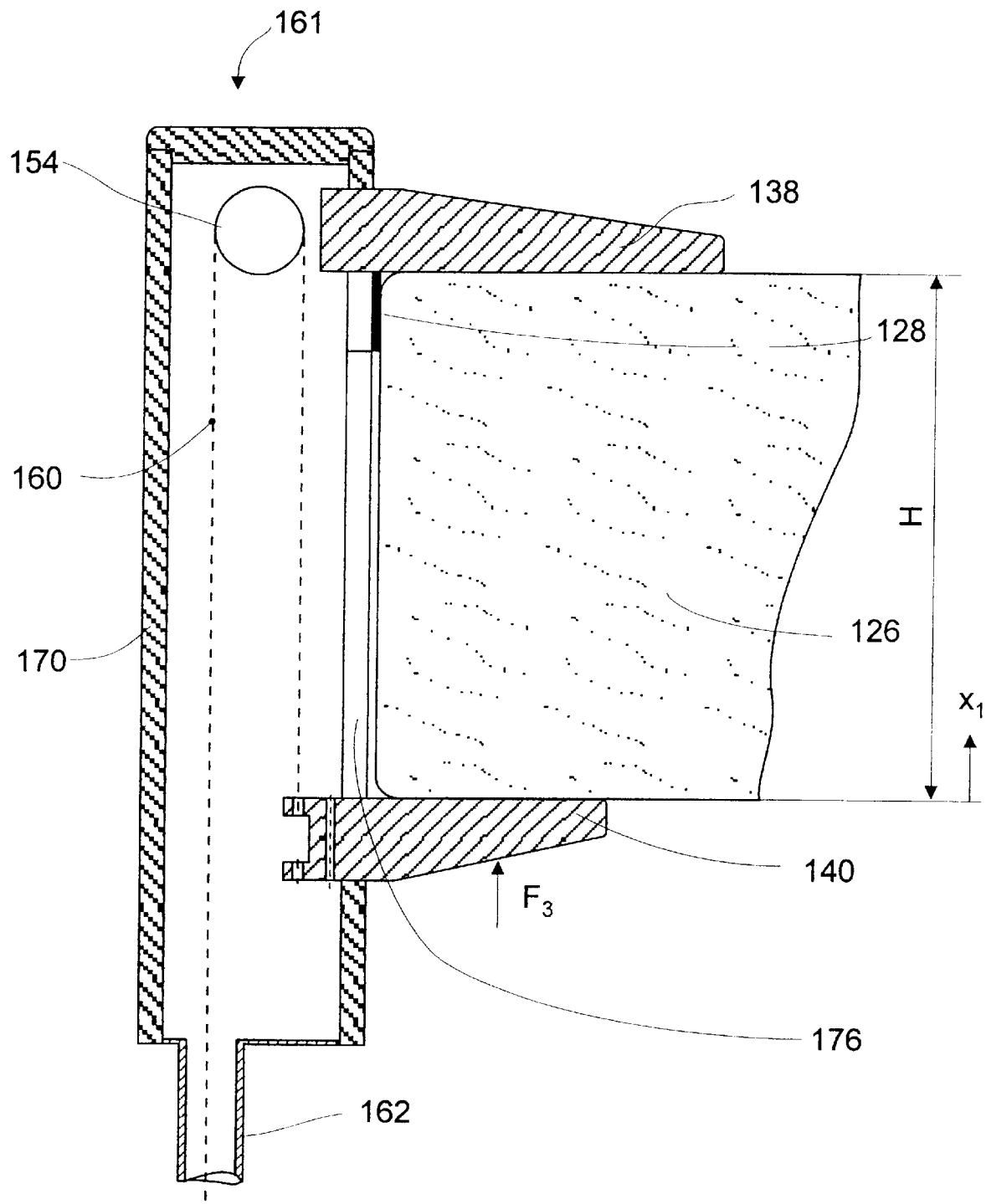
FIGS. 12 and 13 are diagrams of a third embodiment of a linear caliper and hydraulic system.
Figure 13:
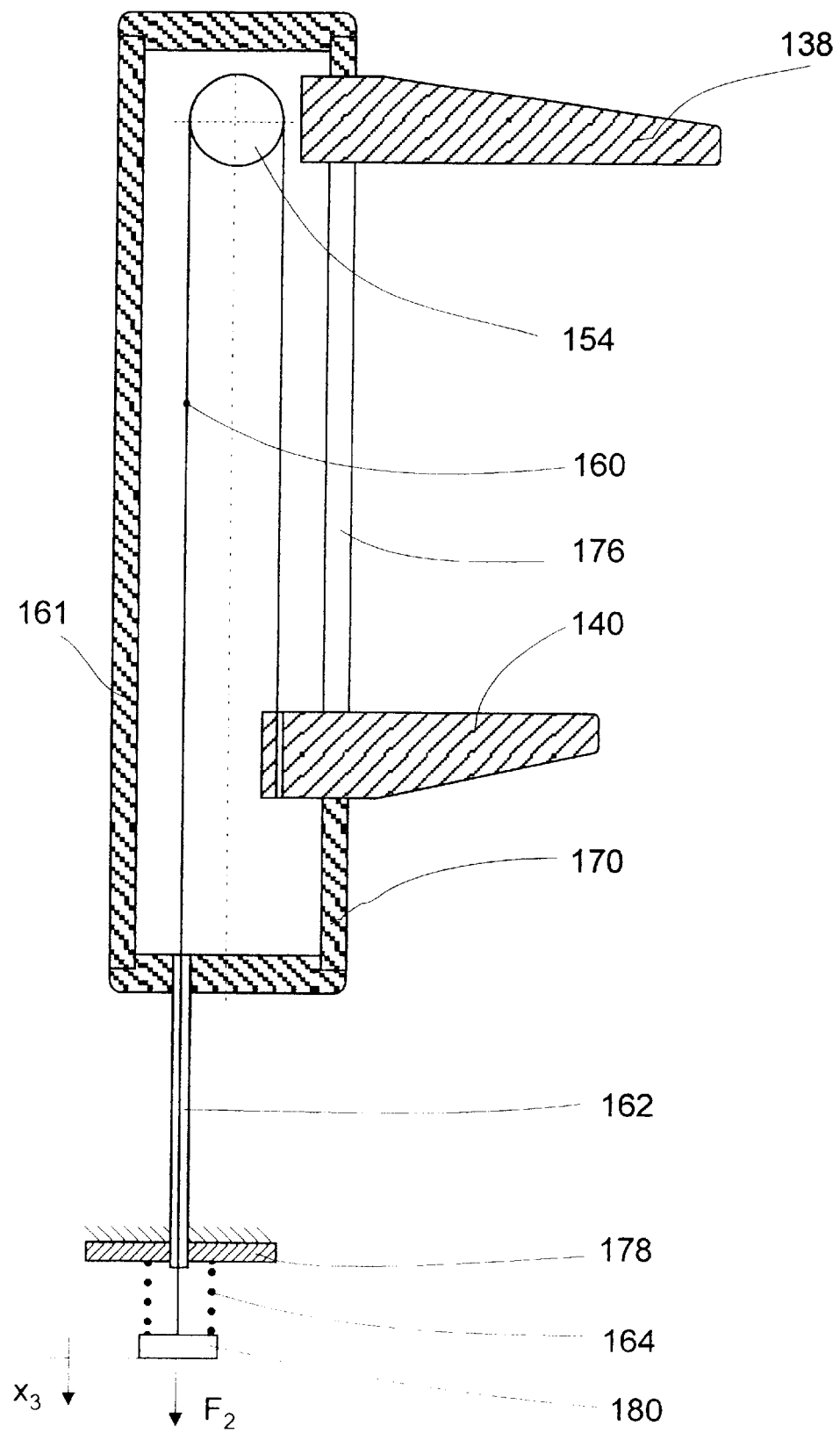

FIGS. 12 and 13 illustrate a third embodiment of a linear caliper 161. In this embodiment, a flexible cable 160 in a jacket 162 are utilized to transmit force and displacement. A force F2 is applied by a spring 164, which is mounted between a fixed surface 178 and a non-fixed surface 180. Force F2 is transmitted by jacketed cable 162 to caliper arm 140, thus loading linear caliper 161 with a constant closing force F3. In this embodiment, a negatively directed movement -X3 does not open caliper arm 140.

The cervical tissue stretches during contractions, due to the pressure applied to the cervix by the fetal head. This results in a transient increase in the diameter of cervix 126, and can unpredictably influence the results of dilation and effacement measurement. Therefore, so as to increase accuracy, it is desirable to regard only measurement data that is acquired between contractions as being accurate. This can be achieved by referring only to the minimal dilation value registered during a defined period of time, or by synchronizing the effacement and dilation measurements with uterine contractions, which are monitored by standard uterine contraction monitor 116.

In an alternative embodiments of the invention, particularly for non-obstetric uses, membrane 128 is fixed to the surface being measured by means other than a clamp, such as by a balloon that is inflated so as to press membrane 128 against the curved surface, or by a human finger. Utilization of an inflatable balloon is particularly suitable for diameter measurements being performed within a hollow cavity.

In summary, then, control unit 102 controls the operation of probe 100 and process the signals of the different sensors that are built into probe 100. It thus performs the following functions:

1) It applies a uniform clamping force to cervix 126 via hydraulic piston 147.
2) It measures the movement of hydraulic piston 147. This movement mirrors the movement of linear caliper 143, 145, or 161 that is attached to cervix 126. This data is then relayed to computer 104 or 124.
3) It momentarily changes the clamping force and measures the resultant new shortening of cervix 126. This is done by momentarily loading hydraulic piston 147 with a second spring 202. Spring 202 can be withdrawn until this moment by a tightening motor operated screw 206. This data is then relayed to computer 104 or 124.
4) It processes the deflection data for flexible membrane 128. This data is then relayed to computer 104 or 124.

Computer 104 or 124 receives data from control unit 102, and performs the following functions:

1) It processes all the acquired data, calculating and charting actual cervical dilation, effacement and consistency.
2) It displays all data.
3) It transmits data to the hospital (via modem) from off-hospital sites.
4) It receives data from other monitoring and database systems.
5) It accesses stored data describing obstetric practice and pathology, and displays such data when appropriate.

There has therefore been described a labor monitoring device which provides continuous, automatic monitoring of cervical dilation and effacement, and allows for intermittent evaluation of cervical consistency, without the need for repeated manual vaginal examinations. As the device is relatively small it does not interfere with commonly performed monitoring and therapeutic procedures, and is comfortable for the patient. The device is easily installed manually at the onset of labor, and does not need to be reinstalled or adjusted thereafter. It is thus safe and easy to use.

The current invention also has potential applications outside of the field of obstetrics. Without departing from the principles of the invention, the device may be used for several other medical applications, some of which are detailed below:

1) The membrane apparatus can be used to measure the inner diameter of hollow organs (such as the uterus) and tube-like organs (such as the intestines, blood vessels, trachea, esophagus, vagina, ureter, and urethra), by using an appropriate attachment system (such as a clamp, a balloon, etc.) for the membrane apparatus. So too, the membrane could be used for measuring the outer curvature of a body part.
2) The linear caliper can be used to measure the thickness of an organ, particularly soft tissues, as is done when measuring skin or fat folds.
3) The double force thickness measurement system can be used for determination of the consistency of any soft organ, such as skin or fat folds, or breast tissue.

The current invention also has potential applications outside of the field of medicine. Without departing from the principles of the invention, the device may be used for several other applications, some of which are detailed below:

1) The membrane apparatus can be used to measure the inner diameter of hollow mechanical parts such as tubes, pipes, round rings, pneumatic or hydraulic cylinders, and internal combustion engine cylinders. It can also be used to measure the local radii of a variable radius curvature part, by using the measuring membrane with an appropriate attachment system (a clamp, a balloon, etc.), or by pressing it in place with the fingers of the operator.

2) A combination of two perpendicular membranes can measure curvatures of 3D objects.

3) A special application is for any of the above cases, in circumstances where the use of electricity is prohibited for safety or other reasons. As measurements are performed by specially treated optical fibers, and the data transmitted via an optical fiber—no electricity is required.

4) The linear caliper mechanism can measure the thickness of any workpiece under test, particularly soft materials (such as measurement of the dimensions of rubber and sponge). A special application is for cases where the use of electricity is prohibited for safety or other reasons. As the data is transmitted via a hydraulic tube—no electricity is involved at the point of measurement.

5) The double force—thickness measurement technique can be used for determination of compression of flexible objects such as springs, rubber, sponges, and the like. As mentioned above, the measurements are performed without the use of electricity at the point of measurement.

What is claimed is:

1. A cervical dilation, effacement, and consistency monitoring system, comprising
   (a) a membrane, operative to flex in accordance with a curvature of a cervix; and
   (b) a first sensor, operative to sense a degree of flexion of said membrane and generate a first signal describing said degree of flexion.

2. The system of claim 1, further comprising
   (c) a caliper having two arms, disposable such that said arms straddle a thickness of a uterine cervical wall; and
   (d) a remote caliper displacement indicator, operative to indicate at a location remote from said caliper, a displacement between said arms.

3. The system of claim 2, further comprising
   (e) a second sensor, operative to sense said indicated displacement and generate a second signal describing said indicated displacement.

4. The system of claim 3, further comprising
   (f) a processor, operative to process said first signal so as to generate a parameter describing a degree of uterine cervical dilation, and operative to process said second signal so as to generate a parameter describing a degree of uterine cervical effacement;
   (g) a memory unit operative to store obstetric data, including a range of normal values and patterns for uterine cervical dilation and effacement during labor; and
   (h) a display, operative to display said parameters and said obstetric data.

5. The system of claim 1, wherein said membrane comprises stainless steel.

6. The system of claim 1, wherein said first sensor is a fiber-optic shape sensor.

7. The system of claim 2, wherein said caliper includes a linear caliper.

8. The system of claim 2, wherein said remote caliper displacement indicator is executed as a hydraulic piston mechanism.

9. The system of claim 2, wherein said remote caliper displacement indicator is further operative to control a force applied to said thickness of said uterine cervical wall by said arms of said caliper.

10. The system of claim 3, wherein said second sensor includes a linear variable differential transformer.

11. The system of claim 4, wherein said processor is further operative to calculate whether said parameters fall outside said range of normal values and patterns, and wherein said display is further operative to depict a warning signal when said parameters are calculated to fall outside said range of normal values and patterns.

12. A method for measuring uterine cervical dilation, effacement, and consistency, comprising the steps of
   (a) providing a membrane, operative to flex in accordance with a curvature of a cervix, and fixing said membrane onto a surface of the cervix;
   (b) sensing a degree of flexion of said membrane;
   (c) generating a first signal describing said degree of flexion; and
   (d) processing said first signal so as to generate a parameter describing a degree of uterine cervical dilation.

13. The method of claim 12, further comprising the steps of
   (e) providing a caliper having two arms, disposable such that said arms straddle a thickness of a uterine cervical wall;
   (f) applying a first force to said thickness of said uterine cervical wall by said arms of said caliper; and
   (g) indicating, at a location remote from said caliper, a first displacement between said arms.

14. The method of claim 13, further comprising the step of
   (h) sensing said indicated displacement;
   (i) generating a second signal describing said indicated displacement; and
   (j) processing said second signal, so as to generate a parameter describing a degree of uterine cervical effacement.

15. The method of claim 14, further comprising the step of
   (k) displaying said parameters.

16. The method of claim 15, further comprising the steps of
   (l) providing obstetric data, including a range of normal values and patterns for uterine cervical dilation and effacement during labor;
   (m) calculating whether said parameters fall without said range of normal values and patterns; and
   (n) displaying a warning signal whenever said parameters are calculated to fall without said range of normal values and patterns.

17. The method of claim 15, further comprising the steps of
   (l) applying a second force to said thickness of said uterine cervical wall by said arms of said caliper; and
   (m) indicating, at a location remote from said caliper, a second displacement between said arms, said indication of said second displacement being chronologically synchronized with said application of said second force.

18. The method of claim 17, further comprising the steps of
   (n) sensing said indicated second displacement;

(o) generating a third signal describing said indicated second displacement;

(p) processing said second signal and said third signal to calculate a parameter describing a cervical consistency; and (q) displaying said parameter.

19. The method of claim 18, wherein said calculation of said parameter describing a cervical consistency includes calculating a difference between said second and third displacements, and a difference between said first and second forces.

20. A cervical dilation, effacement, and consistency monitoring system, comprising (a) a membrane, operative to flex in accordance with a curvature of a cervix, wherein said membrane is a pliable sheet; and (b) a first sensor, operative to sense a degree of flexion of said membrane and generate a first signal describing said degree of flexion.

* * * * *